(12) United States Patent
Ferguson (10) Patent No.: US 9,707,707 B2
(45) Date of Patent: *Jul. 18, 2017

(54) COMFORTABLE MEDICAL HEADLAMP ASSEMBLY

(71) Applicant: Riverpoint Medical, LLC, Portland, OR (US)

(72) Inventor: John Thomas Ferguson, Portland, OR (US)

(73) Assignee: RIVERPOINT MEDICAL, LLC, Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/080,658

(22) Filed: Mar. 25, 2016

(65) Prior Publication Data

US 2016/0207228 A1    Jul. 21, 2016

Related U.S. Application Data

(63) Continuation-in-part of application No. 14/057,351, filed on Oct. 18, 2013, now Pat. No. 9,351,799.

(51) Int. Cl.

| | |
|---|---|
| *F21V 21/084* | (2006.01) |
| *B29C 39/10* | (2006.01) |
| *A61B 90/35* | (2016.01) |
| *A61B 1/06* | (2006.01) |
| *B29C 70/72* | (2006.01) |
| *A61B 90/30* | (2016.01) |

(Continued)

(52) U.S. Cl.
CPC ............ *B29C 39/10* (2013.01); *A61B 1/0692* (2013.01); *A61B 90/30* (2016.02); *A61B 90/35* (2016.02);

(Continued)

(58) Field of Classification Search
CPC .......... A61B 19/5202; A61B 2019/262; A61B 2019/521; F21V 21/084; F21V 33/0068; B29C 70/72

(Continued)

(56) References Cited

U.S. PATENT DOCUMENTS

| | | |
|---|---|---|
| 2,757,574 A | 8/1956 | Thorburn |
| 3,830,230 A | 8/1974 | Chesler |

(Continued)

FOREIGN PATENT DOCUMENTS

KR    1020110095674 A1    8/2011

*Primary Examiner* — Andrew Coughlin
*Assistant Examiner* — Jessica M Apenteng
(74) *Attorney, Agent, or Firm* — Timothy E. Siegel Patent Law, PLLC; Timothy E. Siegel (57) ABSTRACT

A battery headlamp assembly that includes a light engine bezel, an adjustable linkage supporting the bezel and including an electrically conductive system terminating at the bezel. Also, a headband assembly supports the adjustable linkage and includes a longitudinal rigid-flex circuit assembly. This assembly has a strip of rigid-flex circuit having two longitudinally opposed ends and including battery contacts on the ends. Also, two networks of electrical components are each supported by and electrically connected together, and to one of the battery contacts, by the strip of rigid-flex circuit, which includes conductive traces connecting both the networks to the electrically conductive system and to each other, to power the bezel from the battery contacts and to permit communications between the networks. In addition, a further electrically conductive element, electrically connects at least one conductive trace of the rigid-flex circuit to the electrically conductive system of the adjustable linkage.

11 Claims, 7 Drawing Sheets

(51) Int. Cl.
  *B29K 77/00* (2006.01)
  *B29L 31/34* (2006.01)
  *A61B 90/50* (2016.01)
(52) U.S. Cl.
  CPC ............ *B29C 70/72* (2013.01); *F21V 21/084* (2013.01); *A61B 2090/309* (2016.02); *A61B 2090/502* (2016.02); *B29K 2077/00* (2013.01); *B29L 2031/34* (2013.01)
(58) Field of Classification Search
  USPC .................................................. 362/105, 106
  See application file for complete search history.

(56) References Cited

U.S. PATENT DOCUMENTS

| | | | |
|---|---|---|---|
| 5,438,698 A | 8/1995 | Burton et al. | |
| 5,926,320 A | 7/1999 | Parkyn, Jr. et al. | |
| 6,896,389 B1 | 5/2005 | Paul | |
| 7,192,151 B2 | 3/2007 | Clupper et al. | |
| 7,210,810 B1 | 5/2007 | Iversen et al. | |
| 7,737,194 B2 | 6/2010 | Kashiwagi et al. | |
| 7,847,302 B2 | 12/2010 | Basin et al. | |
| 8,337,036 B2 * | 12/2012 | Soto | A42B 3/04 362/103 |
| 9,351,799 B2 | 5/2016 | Ferguson et al. | |
| 2005/0117327 A1 | 6/2005 | Gupta | |
| 2005/0243558 A1 | 11/2005 | Van Duyn | |
| 2006/0285316 A1 | 12/2006 | Tufenkjian et al. | |
| 2007/0097702 A1 | 5/2007 | Crowder | |
| 2007/0097703 A1 | 5/2007 | Goldfain | |
| 2008/0130272 A1 * | 6/2008 | Waters | A42B 1/244 362/106 |
| 2009/0207617 A1 | 8/2009 | Merchant et al. | |
| 2010/0313335 A1 | 12/2010 | Waters | |
| 2012/0120635 A1 | 5/2012 | Strong et al. | |

* cited by examiner

COMFORTABLE MEDICAL HEADLAMP ASSEMBLY

RELATED APPLICATIONS

This application is a continuation-in-part of application Ser. No. 14/057,351, filed Oct. 18, 2013, hereby incorporated by reference as if fully set forth herein.

BACKGROUND

A medical headlamp assembly is a critical part of the surgeon's suite of tools, as it is of great importance that a surgeon can clearly see the operating theater. The ideal headlamp would be light and comfortable to wear for at least four hours and would have battery power sufficient to last four hours off one charge. Further the ideal headlamp assembly would create a bright beam of light homogenous and uniform in brightness and color edge to edge directly along the surgeon's line of sight, without obscuring his or her line of sight. Also, it would be entirely silent, easily adjustable in position and would not be susceptible to infection by mold or any other sort of organism.

For prior art medical headlamp assemblies in which the batteries are mounted on the headband, there has been an issue with comfort in the region where the batteries have been mounted, typically directly over the ears or suspended at the back of the head. The batteries have been separated from the headband itself by circuitry or layers of plastic and fasteners. Because this causes the batteries to protrude farther from the headband, a more rigid polymer has been used in this region to prevent the pull of gravity from causing the batteries to flex the headband around its longitudinal axis, and also to provide a more rigid structure to support the area where the battery is seated. This more rigid polymer potentially causes some discomfort for a lengthy surgery wear-time.

In addition prior art headbands having a housing created from separate elements that were fastened together in the manufacturing process suffered from the presence of seams that served as a difficult-to-clean area where fungal growth could gain a foothold. These seams could also serve as a place where cleaning agents used in an effort to prevent fungal growth and generally prevent contamination could work their way into the interior cavities of the headband, potentially damaging electrical components.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first separate aspect, the present invention may take the form of a battery headlamp assembly that includes a light engine bezel, an adjustable linkage supporting the bezel and including an electrically conductive system terminating at the bezel. Also, a headband assembly supports the adjustable linkage and includes inner assembly. The inner assembly has a strip of flex circuit having two longitudinally opposed ends and defining a set of conductive traces. Also, a pair of circuit boards, each one electrically and physically connected to one of said two longitudinally opposed end, each bear a network of electrical components and include a set of battery contacts The conductive traces connect both the networks to each other to permit communications between the networks. In addition, a further electrically conductive element, electrically connects at least one conductive trace of the flex circuit to the electrically conductive system of the adjustable linkage, to permit the bezel to be powered from the battery contacts.

In a second separate aspect, the present invention may take the form of a method of making a headband for an electrical device to be supported and supplied with electricity by the headband, that utilizes an inner assembly, including an electrically conductive assembly, including a terminal to permit connection to the electrical device and two networks of electrical components each supported by and electrically connected together, to one of the battery contacts and to the electrical terminal by the electrically conductive assembly, and protective cans placed over the networks. The rigid-flex circuit assembly is suspended inside a mold, which is filled with a curable resin, thereby substantially covering the inner assembly with the resin and the resin is permitted to cure.

In a third separate aspect, the present invention may take the form of a battery headlamp assembly that includes a light engine bezel and an adjustable linkage supporting the bezel, and including an electrically conductive system terminating at the bezel. A headband assembly supports and provides an electrical connection to the adjustable linkage and includes battery contacts and battery slots extending rearwardly from the adjustable linkage, for accepting batteries having electrical contacts matching the headband battery contacts and positioning the batteries so that the electrical contacts mate to the battery contacts. Finally, the battery contacts are positioned at least a 14 cm distance from the adjustable linkage, so that on a user of average head size the batteries are positioned mostly behind the user's ears.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced drawings. It is intended that the embodiments and figures disclosed herein are to be considered illustrative rather than restrictive.

DETAILED DESCRIPTION OF THE PREFERRED EMBODIMENTS

Figure 1:
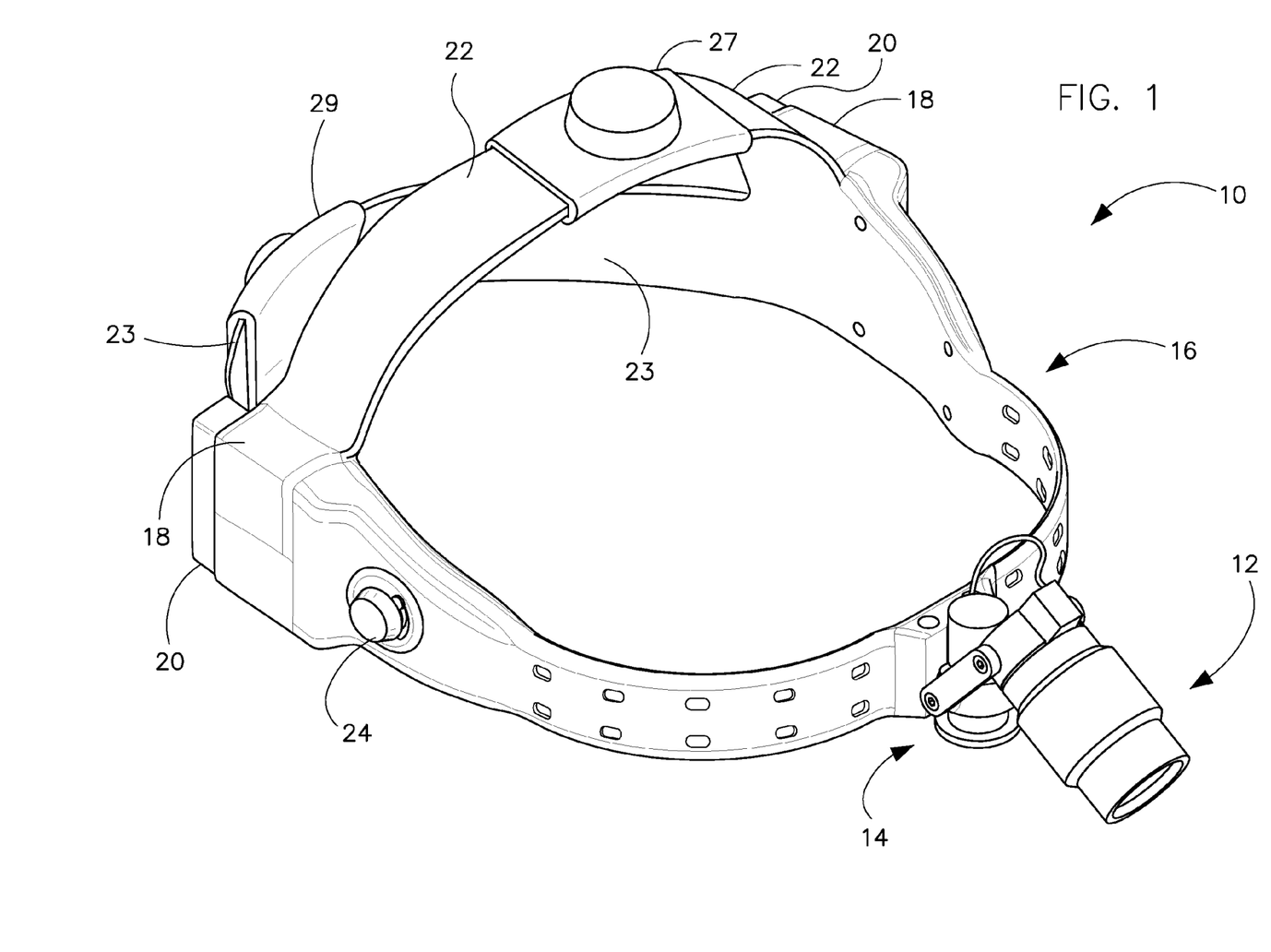
FIG. 1 is an isometric side-top view of a medical headlamp assembly according to the present invention, configured to be received onto a user's head.
Figure 2:
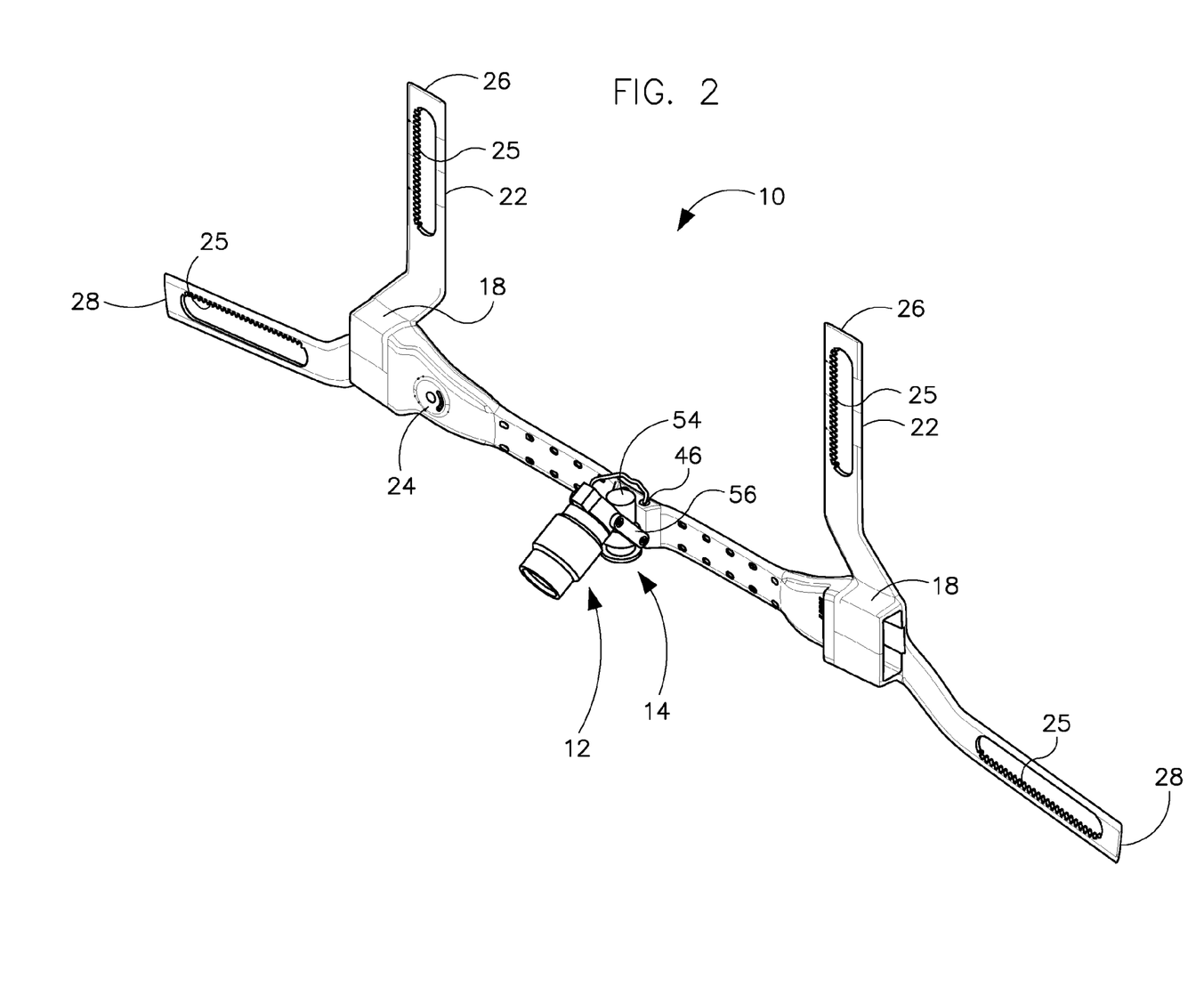
FIG. 2 is an isometric side-top view of the assembly of FIG. 1, but without the tightness adjustment elements, and with elements extended outwardly, in a plane.
Figure 3:
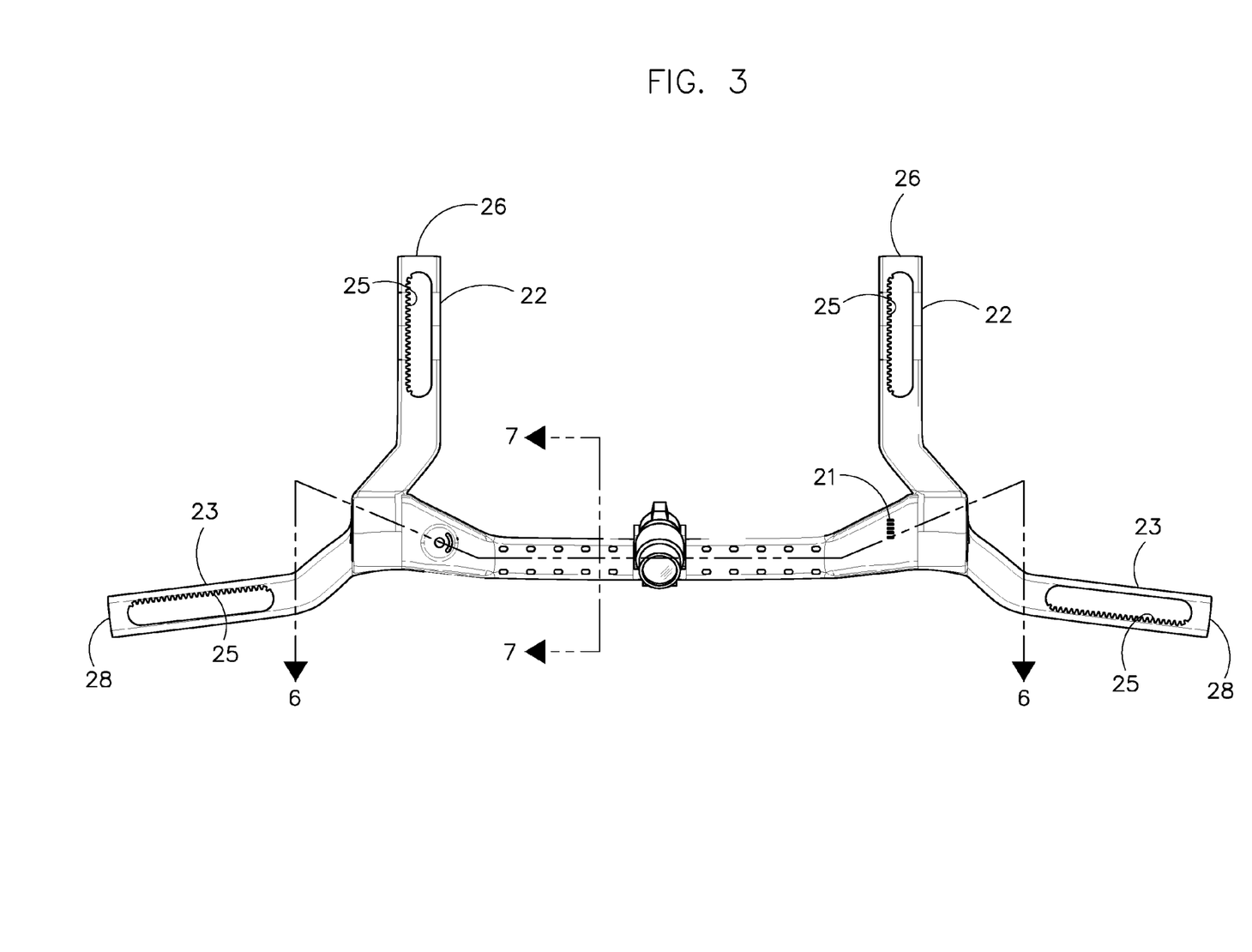
FIG. 3 is a front view of the assembly of FIG. 2.
Figure 4:
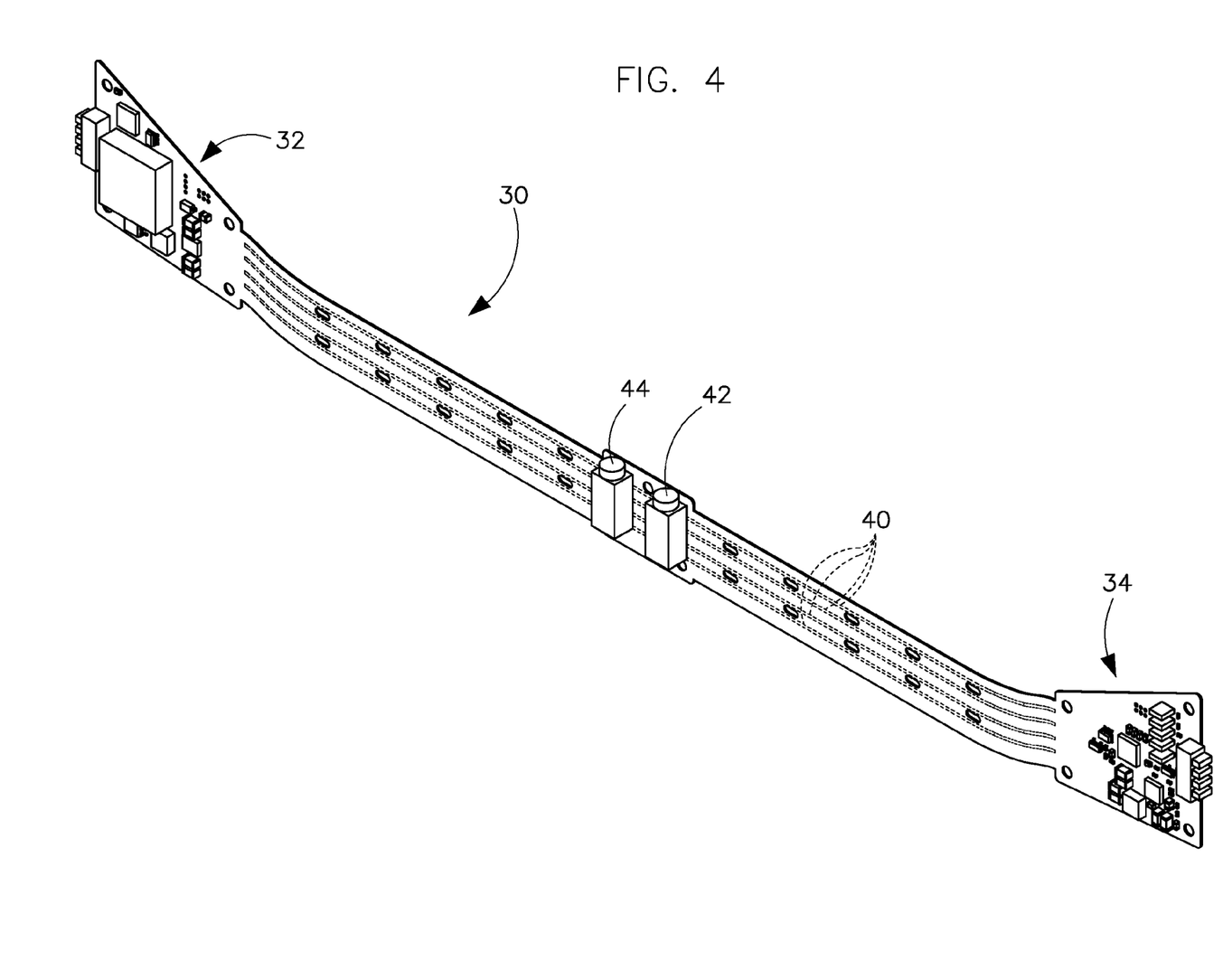
FIG. 4 is an isometric side-top view of a rigid-flex circuit element of the assembly of FIG. 2.
Figure 5:
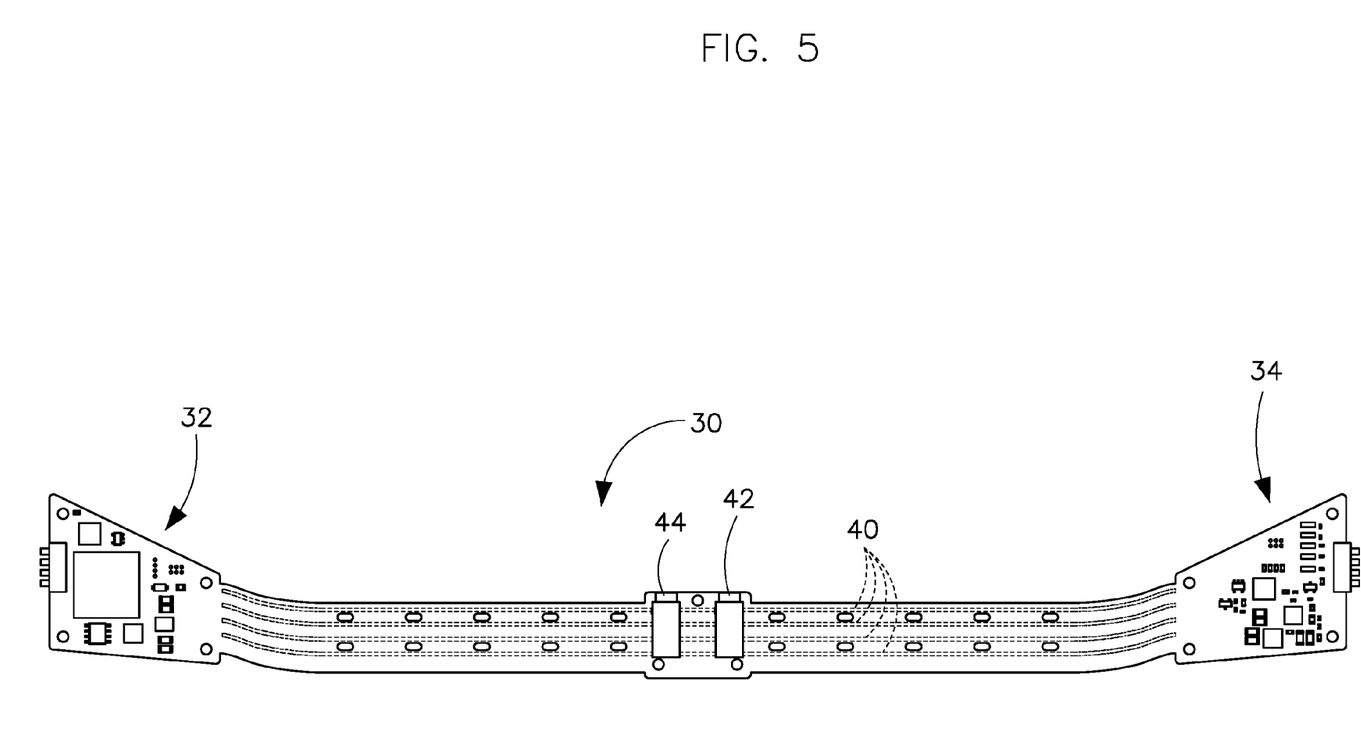
FIG. 5 is a front view of the rigid-flex circuit element of FIG. 4.
Figure 6:
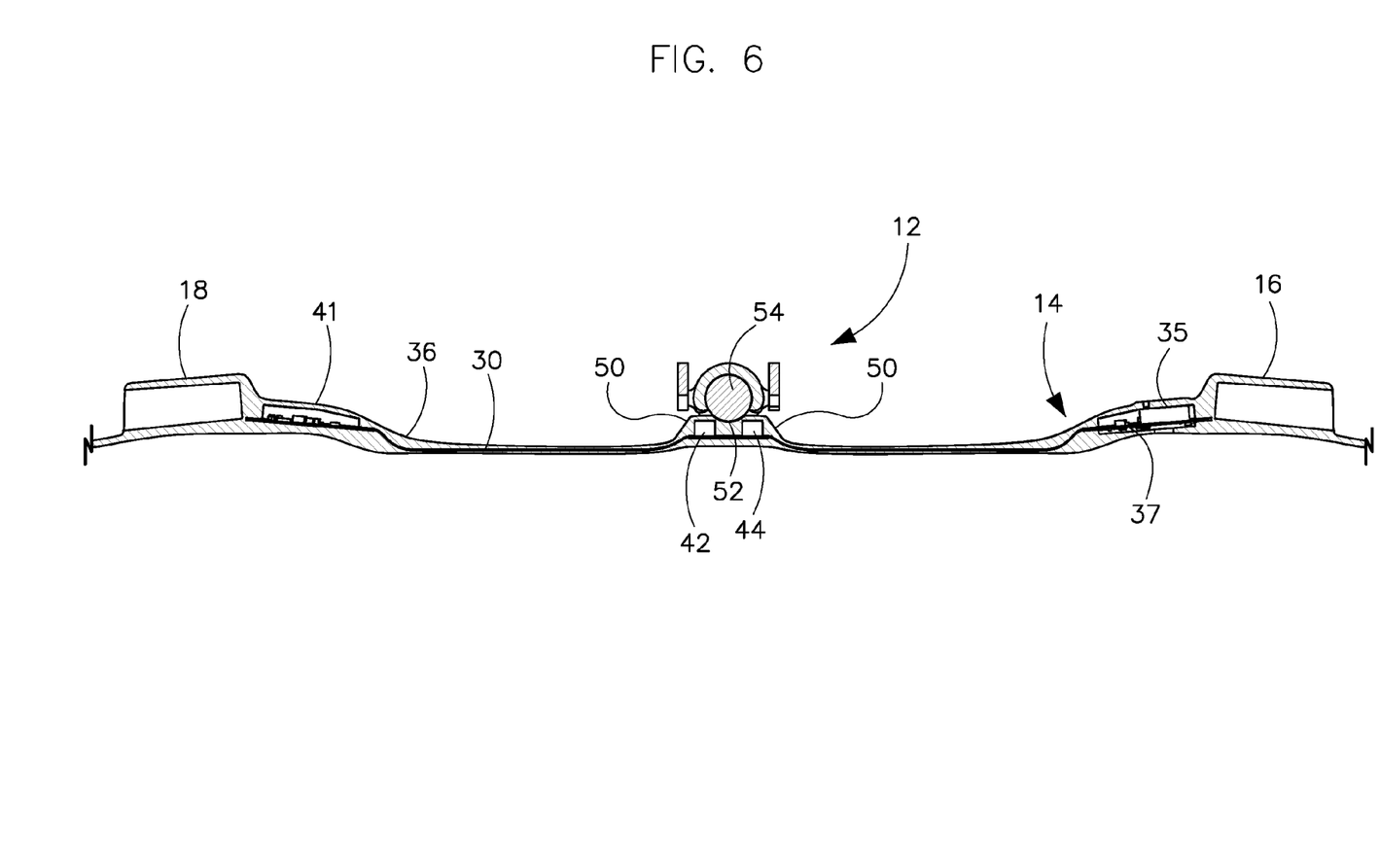
FIG. 6 is a section view of the assembly of FIG. 3, taken along view line 6-6 of FIG. 3.
Figure 7:
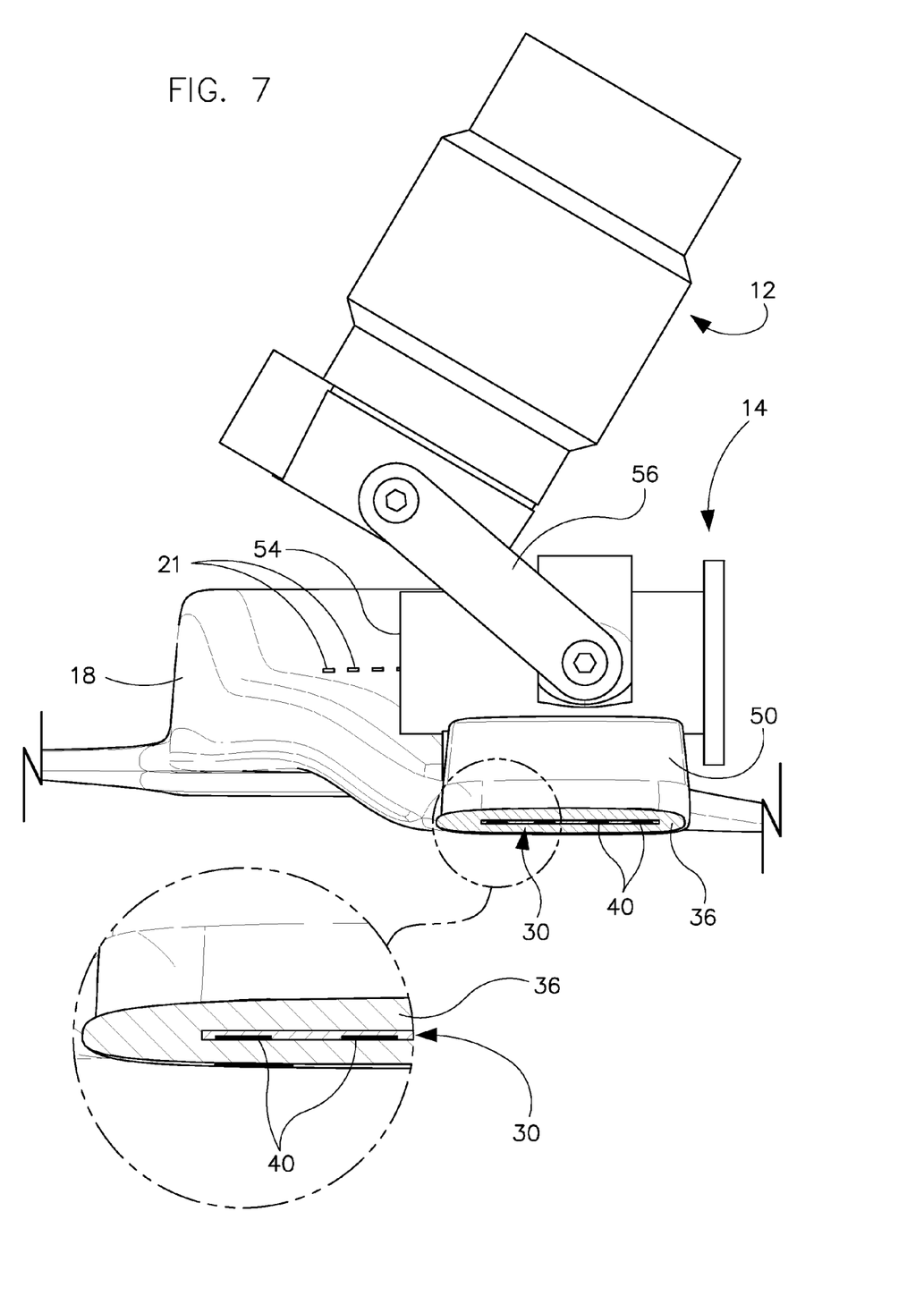
FIG. 7 is a section view of the assembly of FIG. 3, taken along view line 7-7 of FIG. 3.

Referring to FIGS. 1 and 2, in a preferred embodiment of the present invention is a medical headlamp assembly 10, having a light engine bezel 12, an adjustable bezel support linkage 14, a headband assembly 16, defining a pair of battery sockets 18, bearing batteries 20, each in contact to a rigid-flex circuit insert 30 (FIG. 4). The charge remaining in batteries 20 is indicated by a set of battery charge indicator lights 21. A head-top strap 22 and a head-back strap 23 form a part of headband assembly 16. As shown in FIG. 2 straps 22 and 23 are both formed from a pair of arms (26, 28) each having a serrated elongated opening 25. The two arms of the head-top band are drawn together by tightness adjust 27 which engages the serrations to adjust the length of the coupled arms, and the two arms of the head-back strap 23 are drawn together by tightness adjust 29. A brightness control knob 24 is also supported by headband assembly 16.

Referring now to FIG. 3-7 a rigid-flex circuit 30 is embedded into the center portion of headband assembly 16. Rigid-flex circuit is an industry term that describes a structure having both rigid and flexible portions, constructed by laminating together rigid and flexible layers and then removing the rigid layers in areas where flexibility is desired. In this application, the term "flex circuit" encompasses rigid-flex circuit, so that rigid-flex circuit is a type of flex circuit. Rigid-flex circuit 30 includes right and left-side rigid portions that support a right hand electrical network 32, and a left hand electrical network 34, respectfully. The electrical components of network 32 and 34 are connected together by a first set of conductive traces (not shown) that are internal to rigid-flex circuit 30. These traces are configured in a pattern designed to effect a predetermined scheme of connection. Rigid-flex circuit includes an additional rigid portion, right at the location where the linkage 14 connects to headband assembly 16.

The right hand network 32 is kept in an air pocket, protected by a right hand top can 35 (FIG. 6) and a right hand bottom can 37 (FIG. 6), both made of stainless steel that is 0.15 mm thick. The top can 35 is 4.5 mm high, whereas can 37 is 1.5 mm high. During the molding process, these cans 35 and 37 prevent the polymer material from contacting the components of network 32. Although bottom can 37 does create an area of some rigidity to the outside of strap assembly 16, it is covered by a 0.3 mm thick covering of relatively soft polymeric material 36, which greatly ameliorates this condition. A round indent (not shown) in can 37, which defines a hole (not shown) at its center, provides a seat for the head of a shaft (not shown) for the brightness control knob 24. On the left hand side, only a top can 41 (FIG. 6), having similar dimensions to and made of the same material as the top right hand top can 35, is required, due to a smaller component set, confined to the top of rigid-flex circuit 30.

In an alternative preferred embodiment, epoxy resin is applied at the boundaries of some components to seal them against the polymeric material that is injected during the molding process. If the polymeric material is forced between the component and the rigid-flex circuit 30, it can cause problems. The epoxy can be applied by a printer having a movable print head that controllably applies epoxy through a nozzle, in much the same manner as an ink jet printer. This epoxy sealing eliminates the need for the cans 35, 37 and 41, described above. This, in turn, avoids the problem of cans 35, 37 and 41 causing undesirable rigidity in the headband assembly 16. In another embodiment a Macromelt® molding process is used, in which a low pressure polyamide sealing layer is molded over the components, prior to polymer material 36 being molded over the headband elements, including flex circuit 30 and right hand network 32 and left hand network 34. The Macromelt® molding process is available from Henkel Corporation of Rocky Hill, Conn.

Electrical networks 32 and 34 are electrically connected together and to bezel 12 by a second set of conductive traces 40, each of which extends either across the center of rigid-flex circuit 30 or from one of the electrical networks 32 and 34 to either a first jack 42 or a second jack 44. In a preferred embodiment first jack 42 accepts a plug 46 that supplies bezel 12 and second jack 44 accepts a plug (not shown) from a voltage source, for recharging batteries 20. Plug 46 and the wire attached to it may be considered an electrically conductive system of linkage 14, whereas first jack 42 may be considered a further electrically conductive element of headband assembly 16. Bezel 12 could be electrically connected to headband assembly 16 by a simple wire, in which case the portion of the wire in the linkage could still be considered an electrically conductive system and the portion in the headband could be considered a further electrically conductive element.

In an alternative preferred embodiment, rigid-flex circuit 30 is replaced by a longitudinal flex circuit or a longitudinal rigid-flex circuit having a circuit board electrically and physically connected to either end, a right hand circuit board supporting and electrically connecting network 32 and a left had circuit board supporting and electrically connecting network 34. In alternative preferred embodiments the pair of circuit boards are connected by a cable harness or a ribbon cable.

In a preferred embodiment, rigid-flex circuit 30 (together with jacks 42 and 44 and networks 32 and 34) is encased in a sheathing of polymer material 36 that also forms the top arms 26 and side arms 28. To produce the headband assembly 16, rigid-flex circuit 30 is suspended in a mold by shafts that extend through apertures for battery charge indicator lights 21. Polymer material in liquid phase is forced into the mold and after it has been allowed to cure, the shafts are withdrawn and the headband assembly 16 is ejected.

In a preferred embodiment sheathing polymer material 36 may be Styrene-Ethylene/Butylene-Styrene Block Copolymer or similar material, preferably having a shore durometer rating of between 50 and 60 in its cured state. In one preferred embodiment, the shore durometer rating is 55. The 100% modulus is preferably between 1800 and 2500 psi. The mold injection temperature is between 180° C. and 240° C. These materials are available from United Soft Plastics of Lawrenceville, Ga.

In prior art, battery bearing headbands, the battery sockets have been separated from the material contacting the user's head by a space for circuitry, whereas in the preferred embodiment, the circuitry has been placed in front of the battery, as opposed to a position interposed between the battery and the head. Also, the battery sockets 18 have been moved farther back on the head, relative to prior art headbands, so that the closest portion of the batteries 20 to the linkage is 153 mm from the linkage as measured along the headband as it curves about the head, or stated in a slightly different but equivalent manner, measured as it would be if the headband assembly were laid out flat. For most wearers, this places the forwardmost part of the batteries at a position just above the ears, so that a portion of batteries may extend in backward direction at the place where the head curves inwardly toward the back, thereby avoiding contact between the batteries and the head, and providing a greater balance in weight, yielding greater comfort.

There are a number of advantages to the resulting headband. First, as it is constructed as a unitary piece, there are no seams that in other systems provide a foothold for the growth of fungus, and seepage of users' cleaning fluid into interior cavities, which can potentially damage electrical networks 32 and 34. Also, in one prior art system the two pieces that were joined to form the band for the back of the head also formed the panels separating the batteries from the head. This piece was made of a harder polymer material than other portions of the headband, in part to resist the tendency of the batteries, which extended further from the head because of the interposed electrical network, to torque with the top being pulled by gravity downwardly, which could easily translate to away from the head. The use of a harder polymer, however, can result in discomfort over the hours required to complete some surgeries. In headband 16, the use over the entire assembly of polymer material 36 which in a preferred embodiment has a shore durometer reading of 55 is more comfortable, even over long periods of time. In addition, the traces 40 that link networks 32 and 34 permit communication that permits these networks to cooperate. In one preferred embodiment, the battery delivering power to the bezel 12 shifts periodically, for example as the voltage of the active battery passes below a threshold, the load of the optical assembly is shifted to the other battery 20, so that the batteries drain at the same rate, over time. Also, those traces leading from networks 32 and 34 to the jack for supplying bezel 12 make external wires unnecessary. Such wires can present a snagging hazard.

A pair of parallel front-center vertical ridges 50 are created by the encasement of jacks 42 and 44. The valley 52 between these ridges, form an elongated seat for post 54, which is part of support linkage 14. When arms 56 (also part of linkage 14) are rotated, post 54 is torqued and in turn torques headband assembly 16. The structure of post 54 and ridges 50, however, help to diffuse this torque and material 36 helps to cushion the forehead from the torque, so that the operation of rotating arms 56 is not as uncomfortable to the wearer of headlamp assembly 10 as it would otherwise be.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:
1. A method of making a headband for an electrical device to be supported and supplied with electricity by said headband, comprising:
 (a) providing an inner assembly, including:
  (i) an electrically conductive assembly, including a terminal to permit connection to said electrical device, and including battery contacts; and
  (ii) two networks of electrical components each supported by and electrically connected together, and connected to one of said battery contacts and to said electrical terminal by said electrically conductive assembly;
 (b) suspending said inner assembly inside a mold and filling said mold with a curable resin, thereby substantially covering said inner assembly with said resin; and
 (c) permitting said resin to cure.

2. The method of claim 1, wherein said electrical terminal is at the center of said inner assembly.

3. The method of claim 1, wherein said electrically conductive assembly includes a longitudinal extent of flex circuit that supports as well as electrically connects said networks.

4. The method of claim 1, wherein said terminal is a jack supported by said flex circuit.

5. The method of claim 1, wherein said curable resin is a polymer resin.

6. The method of claim 5, wherein said polymer resin is a styrene-ethylene/butylene-styrene block copolymer.

7. The method of claim 1, further including the step of sealing at least some of said electrical components, to prevent polymeric material from entering between said components and said electrically conductive assembly, prior to said step of suspending said inner assembly in a mold and filling said mold with a curable resin.

8. The method of claim 7, wherein said step of sealing is performed using a printer having a position controllable nozzle.

9. The method of claim 7, wherein said step of sealing is done with epoxy.

10. The method of claim 7, wherein said step of sealing is done with a low pressure over mold of polymer material.

11. The method of claim 10, wherein said polymer material is a polyamide.

* * * * *